United States Patent [19]
Nishizawa et al.

[11] Patent Number: 4,626,252
[45] Date of Patent: Dec. 2, 1986

[54] DISPOSABLE DIAPER

[75] Inventors: Kazunori Nishizawa, Funabashi; Hiroshi Mizutani, Yachiyo, both of Japan

[73] Assignee: Kao Corporation, Tokyo, Japan

[21] Appl. No.: 759,923

[22] Filed: Jul. 29, 1985

Related U.S. Application Data

[63] Continuation of Ser. No. 465,693, Feb. 10, 1983, abandoned.

[30] Foreign Application Priority Data

Mar. 2, 1982 [JP] Japan .................. 57-32830

[51] Int. Cl.$^4$ .................................... A61F 13/16
[52] U.S. Cl. ................... 604/370; 604/372; 604/373
[58] Field of Search ............ 428/46, 315.5, 521, 428/500, 523, 220; 128/156; 604/381, 382, 378, 372, 373

[56] References Cited

U.S. PATENT DOCUMENTS 3,881,489  5/1975  Hartwell .................. 604/382
4,308,303  12/1981  Mastroianni et al. ....... 428/315.9

Primary Examiner—C. Fred Rosenbaum
Assistant Examiner—Sherri E. Vinyard
Attorney, Agent, or Firm—Flynn, Thiel, Boutell & Tanis

[57] ABSTRACT

A disposable diaper in which the backing sheet is a porous, vapor-permeable, liquid-impermeable film made by mixing 100 parts by weight of a polyolefin resin with from 28 to 200 parts by weight of filler and from 10 to 70 parts by weight of a liquid or wax-like hydrocarbon polymer, molding the mixture to form a film and then stretching the film uniaxially or biaxially so that its dimension after stretching is more than 1.2 times as large as its dimension prior to stretching.

10 Claims, 1 Drawing Figure

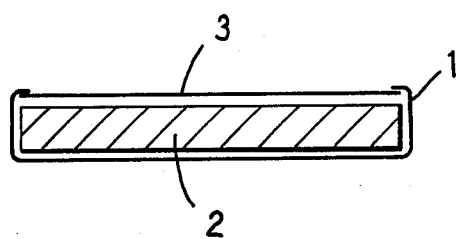

DISPOSABLE DIAPER

This application is a continuation, of U.S. Ser. No. 465,693, filed Feb. 10, 1983 now abandoned.

This invention relates to an improved, integrally formed, disposable diaper. More particularly, it relates to a disposable diaper in which a liquid-impermeable, but vapor-permeable, porous film is used as a leakproof backing sheet.

Hitherto, as the leakproof backing sheet for disposable diapers, there has been used a sheet produced by mixing low-density polyethylene with 3 to 5 wt. % of titanium oxide, molding the mixture to form a film having a basis weight of 20 to 30 g/m$^2$ and then embossing said film. However, because of its vapor impermeability, such a sheet causes a so-called clammy state around the wearer's buttocks because the inside of the diaper becomes exceedingly damp during long-time use. Such a clammy state causes red skin irritation, like prickly heat, on the wearer's skin surface, and if the diaper is worn for a longer time in such a state, the wearer may suffer from a serious case of diaper rash. The necessity of a vapor-permeable leakproof layer for a diaper has been pointed out and proposals have been made concerning utilization of porous films, but there is not yet available a vapor-permeable, liquid-impermeable film which is fully satisfactory in respect of film strength, particularly tear strength, flexibility, economy and moisture permeation.

As a result of extensive studies for solving these problems, the present inventors have discovered the present invention.

BRIEF DESCRIPTION OF THE DRAWING

The drawing is a cross-sectional view of a disposable diaper according to the invention.

Briefly, the present invention provides a disposable diaper comprising an integral assembly of a vapor-permeable, liquid-impermeable, backing sheet 1, an absorbent layer 2 placed thereon and a liquid-permeable sheet 3 overlying said absorbent layer, in which the vapor-permeable, liquid-impermeable, backing sheet is composed of a film produced by mixing 100 parts by weight of a polyolefin resin, 28 to 200 parts by weight of a filler and 10 to 70 parts by weight of a liquid or wax-like hydrocarbon polymer, molding the mixture to form a film and then stretching the film laterally and/or longitudinally until it has a dimension of more than 1.2 times its original dimension in that direction, whereby to form fine pores in the film.

As examples of polyolefin resins usable in this invention, there can be mentioned high-density polyethylene, polypropylene and linear low-density polyethylene resins. These resins can be used either singly or in mixtures of two or more of them, but it is preferred to use a linear low-density polyethylene resin alone or a high-density polyethylene resin alone.

As the filler used in this invention, it is possible to employ both inorganic and organic fillers. Examples of suitable inorganic fillers are calcium carbonate, talc, clay, kaolin, silica, diatomaceous earth, magnesium carbonate, barium carbonate, magnesium sulfate, barium sulfate, calcium sulfate, aluminum hydroxide, zinc oxide, magnesium hydroxide, calcium oxide, magnesium oxide, titanium dioxide, alumina, mica, asbestos powder, glass powder, "Shirasu" (white sandy deposit), zeolite, siliceous china clay and the like. Among them, calcium carbonate, talc, clay, silica, diatomaceous earth and barium sulfate are preferred.

As examples of organic fillers, cellulose powder, such as woodflour or pulp powder, can be used either singly or as a mixture of two or more of them.

The average particle size of the filler used in this invention is preferably less than 30 microns, more preferably less than 10 microns, and most preferably, from 1 to 5 microns. An excessively large particle size causes a poor pore density of the stretched film, while an excessively small particle size results in a bad dispersibility of the filler in the resin and, hence, poor workability.

It is desirable to perform a surface treatment of the filler for the purposes of achieving better dispersibility of the filler in the resin and, also, better stretchability of the film. A treatment of the filler with a fatty acid or a metal salt thereof gives an especially favorable result.

The liquid or wax-like hydrocarbon polymer used in this invention can be selected from liquid polybutadiene, liquid polybutene and hydrogenates of liquid polybutadiene, among which saturated polyhydroxy-substituted hydrocarbons obtained by hydrogenating hydroxy-terminated liquid polybutadienes are preferred.

The saturated polyhydroxy-substituted hydrocarbons are hydrocarbon polymers in which the main chain has at least 1.5 hydroxyl groups per one molecule and which has been saturated or substantially saturated by hydrogenation. Such polymers preferably have a number-average molecular weight (as measured by the vapor pressure method) within the range of 400 to 48,000, preferably 500 to 20,000. An excessively low number-average molecular weight cannot provide satisfactory weather resistance, while an excessively high number-average molecular weight leads to poor fluidity of the polymer which makes it difficult to properly treat the polymer. The average number of hydroxyl groups per one molecule should be 1.5 or more preferably 1.8 or more, most preferably 2.0 to 5.0. It is desirable that the hydroxyl groups are present at the one or both terminals of the main chain or at the terminal of a long side chain.

Such saturated polyhydroxy-substituted hydrocarbons can be obtained by a known method, for example, by hydrogenating a butadiene-based liquid polymer obtained by the radical polymerization of butadiene alone or together with a copolymerizable monomer, by using hydrogen peroxide or the like as polymerization initiator. Isoprene, chloroprene, styrene, methyl acrylate, methyl methacrylate, methyl vinyl ether or the like can be used as the copolymerizable monomer.

Hydrogenation can be accomplished in the usual way by using a nickel catalyst (such as reduced nickel or Raney nickel), a cobalt catalyst, a platinum catalyst, a palladium catalyst, a rhodium catalyst, a ruthenium catalyst or a mixture or an alloy catalyst thereof.

It is considered that the introduction of said hydrocarbon polymer having a polar hydroxyl group at the terminal thereof gives a favorable result in improving the compatibility of the components of the film with each other.

The polyolefin resin can be mixed with a heat and/or ultraviolet stabilizer, a pigment, an antistatic agent, a fluorescent agent and the like according to a conventional method.

As for the proportions of the polyolefin resin, the filler and the liquid or wax-like hydrocarbon polymer, it is recommended that the filler is blended in an amount of 28 to 200 parts by weight and the liquid or wax-like hydrocarbon polymer is blended in an amount of 10 to 70 parts by weight, both based on 100 parts by weight of the polyolefin resin.

If the proportion of the filler is less than 28 parts by weight, sufficient pores are not formed in the stretched film, whereas if the amount of filler exceeds 200 parts by weight, poor kneadability, poor dispersibility and poor film or sheet moldability are obtained, and, also, the stretched product proves to be low in its surface strength.

In producing the leakproof sheet according to this invention, the above-mentioned three materials are mixed and the mixture is molded to form a film or sheet in a known way. Then the film or sheet is stretched more than 1.2 times its original dimension in at least one direction to form fine pores in the film or sheet. In the case of uniaxially stretching said film or sheet, usually roll stretching is preferably employed, but tubular stretching can be used to place particular stress in one direction (take-up direction).

Such stretching can be accomplished in a single stage or in two or more stages.

Usually, the stretch ratio that can provide the desired porosity and uniform stretch is more than 1.2 times, preferably 1.2 to 4.0 times, more preferably 1.2 to 2.0 times, the original dimension in at least one direction of the film.

In the cases of both uniaxial and biaxial stretching, it is possible to precisely stabilize the film by conducting a heat treatment after stretching. It is also possible to perform a known surface treatment, such as corona discharge or flame treatment.

The film or sheet thus obtained is excellent in water vapor and gas permeability, because it has interconnected pores. In use of such a film or sheet as a backing sheet for a disposable diaper, consideration must be given to flexibility, strength and economy, and such factors are greatly affected by the basis weight of the film or sheet. The basis weight is preferably within the range of 20 to 50 g/m$^2$, most preferably 25 to 40 g/m$^2$. From the economical viewpoint, it is desirable that such a basis weight is less than 20 g/m$^2$, but with the presently available techniques, such a low basis weight cannot provide sufficient film or sheet strength for practical use. From the aspect of strength, a basis weight of greater than 50 g/m$^2$ is desirable, but such a high basis weight is impractical in terms of economy and flexibility.

Other constituents of the disposable diaper according to this invention will now be described.

Regarding the absorbent medium, there has long been used a laminate of sheets of tissue paper. More recently, a fluff pulp web wrapped with tissue paper or wet strength tissue paper has become popular for the reasons of mass production and economy. These prior art absorbent media can be employed in the disposable diaper of this invention, but in order to enhance the effect, it is desirable to adopt a new design in which a super absorbent polymer is incorporated in the absorbent medium so that the urine absorbed by said medium will be retained therein, even when the wearer's body weight is loaded thereon. As the super absorbent polymer, it is advantageous to use, for example, Aquakeep by Seitetsu Kagaku KK.

A non-woven fabric is commonly used as the liquid-permeable sheet 3 forming the diaper surface layer that touches wearer's skin. In order to accomplish the object of this invention, it is desirable to employ a liquid-permeable sheet which is so designed as to be capable of preventing the absorbed liquid from again seeping out from the absorbent medium. For this purpose, it is recommended to employ a hydrophobic non-woven fabric principally composed of polyester fiber or polyolefin fiber. Other known techniques, such as those disclosed in Japanese Utility Model Laid-Open No. 11212/1981 and Japanese Patent Laid-Open No. 123745/1977, can be advantageously applied for this purpose.

In addition to the above-mentioned basic structural features, it is also possible to employ other known features such as a pressure sensitive tape as a diaper fixing means and attaching an elastic member for preventing leaking. These means can be readily applied to the disposable diaper of this invention.

The invention will be further described in detail hereinbelow by reference to specific illustrative examples thereof, but these examples do not limit the scope of the invention. In the Examples, the term "%" means percent by weight, unless otherwise noted.

Preparation 1 (Preparation of saturated polyhydroxy-substituted hydrocarbon)

3 kg of commercially available polyhydroxypolybutadiene (R-45 HT produced by Arco Inc., numberaverage molecular weight (Mn)=3,1000; OH group=0.82 meq/g; cis-1,4=15%; trans-1,4=58%; vinyl=27%), 3 kg of cyclohexane and 300 g of a catalyst of ruthenium (5%) supported on carbon (a product by Japan Engelhard Co.) were fed to an autoclave having a capacity of 10 liters, and, after purging the inside of the system with purified argon gas, high-purity hydrogen gas was supplied to the autoclave, with heating being started simultaneously. The steady-state conditions (internal temperature=approx. 100° C.; internal pressure=approx. 50 kg/cm$^2$) were reached in about 30 minutes. The reaction system was left standing under these conditions for about 15 hours and then the hydrogenation reaction was stopped, following which the polymer was refined and dried in the usual way.

The obtained polymer was waxy and IR absorption spectral analysis of it established that it was a saturated hydrocarbon polymer substantially free of double bonds. The -OH group content of the hydrogenate was 0.8 meq/g.

Preparation 2 (Preparation of saturated polyhydroxy-substituted hydrocarbon)

Hydrogenation was carried out in the same way as described in Preparation 1 except that a liquid polybutadiene G-2000 (produced by Nippon Soda KK, molecular weight=2,000) was used as the polyhydroxypolybutadiene. The obtained polymer was liquid and had an iodine value of 5 g/100 g, a hydroxyl value of 44 KOH mg/g and a viscosity of 775 poises at 30° C.

EXAMPLE 1

20 kg of a high-density polyethylene resin (Novatek ER-002, "Novatek" being a registered trademark of Mitsubishi Kasei Kogyo KK) and 5 kg of saturated polyhydroxy-substituted hydrocarbon (the same as obtained in Preparation 2) were stirred and mixed in a Henschel mixer and then 25 kg of calcium carbonate (average particle size: 1.2 microns, treated with a fatty acid) was added thereto, followed by further mixing under stirring.

The mixture thus obtained was additionally mixed and granulated by a double screw mixer DM-65 (mfd. by Nippon Seikojo KK).

The product was subjected to blown-film extrusion using a 40 mm $\phi$ extruder to form a 70 $\mu$ thick film. The extrusion conditions were as follows:
Cylinder temperatures: 170°-190°-210°-230° C.
Die head temperature: 230° C.
Takeup rate: 8 m/min, blow ratio=2.0, flat width =314 mm The obtained film was uniaxially stretched by a roll stretcher under the following stretching conditions:
Stretching temperature: 80° C.
Draw ratio: 2.7 times the original length
Stretching rate: 11.0 m/min The stretched film was sufficiently porous and satisfactorily whitened. It was also uniformly stretched and had a beautiful surface appearance.

By using the obtained porous film as the back sheet, a disposable diaper was made in the following way. A highly absorbent polymer Aquakeep (produced by Seitetsu Kagaku KK) was spread uniformly between layers of fluff pulp at a rate of 70 g/m$^2$, to form an absorbent medium having a basis weight of 300 g/m$^2$. This laminate was wrapped with wet strength tissue paper. The wrapped laminate was placed on the back sheet and was covered by a non-woven fabric (basis weight: 20 g/m$^2$) principally composed of hydrophobic fiber, especially ES fiber (a product of Chisso KK), and finally the components were integrated to form a unitary article with a fastening tape tab attached thereto.

EXAMPLE 2

20 kg of a linear low-density polyethylene resin (Ultzex 2021-NF, "Ultzex" is a registered trademark of Mitsubishi Sekiyu Kagaku Kogyo KK) and 5 kg of saturated polyhydroxy-substituted hydrocarbon obtained in Preparation 1 were stirred and mixed by a Henschel mixer and then 25 kg of calcium carbonate (average particle size: 1.2 microns, treated with a fatty acid) was added thereto, followed by additional mixing under stirring.

The obtained mixture was further mixed and granulated by a double screw mixer DSM-65 (mfg. by Nippon Seikojo KK).

The resulting product was subjected to blown-film extrusion using a 40 mm $\phi$ extruder to form a 70 $\mu$ thick film. The extrusion conditions were as follows:
Cylinder temperatures : 170°-190°-210°-230° C.
Die head temperature: 200° C.
Takeup rate: 8 m/min, blow ratio=2.0, flat width=314 mm The film thus obtained was uniaxially stretched by a roll stretcher under the following conditions:
Stretching temperature: 80° C.
Draw ratio: 2.5 times the original length
Stretching rate: 11.0 m/min The stretched film was porous, satisfactorily whitened and uniformly stretched and also had a beautiful surface appearance.

By using this porous film as a backing sheet, a disposable diaper was made in the same way as described in Example 1.

EXAMPLES 3-7

Porous films were produced by following the procedure of Example 1, but by changing the proportions of high-density polyethylene, filler and saturated polyhydroxy-substituted hydrocarbon as shown in Table 1. By using these porous films as back sheets, disposable diapers were made in the same manner as described in Example 1.

EXAMPLES 8-10

By using the hydrocarbon polymer obtained in Preparation 1, there were produced porous films in the same way as described in Example 1, except that the draw ratio was changed as shown in Table 1, and disposable diapers were formed in the same manner as described in Example 1 by using said respective porous films as back sheets.

EXAMPLES 11-12

Porous films were obtained in the same manner as described in Example 1 except that talc (MS Talc, a product of Japan Talc Co.) or diatomaceous earth were used as fillers. Disposable diapers were formed in the same manner as Example 1 by using said porous films as back sheets.

EXAMPLES 13-15

Porous films were obtained following the process of Example 1, but by changing the proportions of the linear low-density polyethylene, filler and hydrocarbon polymer as set forth in Table 1. Disposable diapers were made in the same way as described in Example 1 by using said porous films as back sheets.

EXAMPLES 16-18

Porous films were produced in the same manner as described in Example 2 by using liquid polybutadiene (Nisso PB-G available from Nippon Soda KK) or liquid polybutene (Nisseki Polybutene HV-300 available from Nippon Sekiyu Kagaku KK) as the liquid hydrocarbon polymer, and using calcium carbonate or talc (MS Talc available from Nippon Talc KK) as the filler. Disposable diapers were formed in the same manner as described in Example 1 by using said porous films as back sheets.

COMPARATIVE EXAMPLES 1-3

Porous films were obtained in the same manner as that described in Example 1 except that no hydrocarbon polymer was blended in the mixture and that the stretching temperature and draw ratio were changed. By using these porous films as back sheets, there were formed disposable diapers by following the procedure of Example 1.

COMPARATIVE EXAMPLES 4-6

Porous films were obtained in the same way as described in Example 2 except that no hydrocarbon polymer was blended in the mixture and that the stretching temperature and draw ratio were changed. Disposable diapers were produced in the same manner as described in Example 1 by using said porous films as back sheets.

The properties of the films obtained in Examples 1-18 and Comparative Examples 1-6, diaper formability and the test results of usage thereof are shown in Table 1. Similar evaluations were also made on a disposable diaper made by using a commercially available back sheet and another disposable diaper made by using two sheets of commercially available ring-shaped diaper of bleached cotton cloth with a commercially available wool flannel and a diaper cover. The results thereof were also shown in Table 1 (Comparative Examples 7 and 8).

The signs used in the column headed "Composition" in Table 1 are defined in Table 2.

The data given in Table 1 were determined by the following methods.

(1) Strength (*a*) Tensile strength:

A test piece measuring 10×140 m/m was placed in the CD direction (lateral direction) of the sample film and pulled at a rate of 300 mm/min at pulling intervals of 100 m/m by using a Tensilon tensile tester, and the maximum load was given as tensile strength.

(*b*) Tear strength:

A 30×60 mm test piece was placed in the stretching direction of the sample film and, by providing a 30 mm slit at the middle part of the shorter side of the test piece, its tensile strength was measured by using the Tensilon tensile tester. The tearing rate was set at 300 mm/min.

(2) Moisture permeability 40 g/m$^2$ fluffed pulp was wrapped with a tissue paper and molded into a 10×10 cm sheet. This sheet was placed on an aluminum plate and then 20 ml of a physiological saline solution was dropped thereonto so that it was spread uniformly over the entire sheet. Then the aluminum plate and sheet were covered with a 12×12 cm sample film and the four sides were secured by a vinyl tape. The prepared test piece was fixed to the wall (acrylic plate) of a constant-temperature water tank kept at 30° C. and, 2 hours later, the changes in the weight was measured. The measurement was conducted under conditions of 20° C. and 60% RH.

(3) Use test

The finished disposable diapers were used by seven baby test subjects for one week continuously (per one test), and the condition of diaper rash and other troubles which developed during the test period were observed. When the test subjects suffered from a diaper rash because of ill health (such as diarrhea attack) in the course of the test, such test subjects were eliminated from the test results. The tests were conducted during the period from June to October.

TABLE 1

| | Composition (*) Polyolefin resin | Filler | Hydrocarbon polymer | Stretching conditions Temperature (°C.) | Stretch ratio | Film thickness (μ) | Strength Tensile strength (g) | Tear strength (g) | Moisture permeability g/100 cm².2 hr | Flexibility | Disposable diaper formability and use test | Remarks |
|---|---|---|---|---|---|---|---|---|---|---|---|---|
| 1 | A-1 40 | D-1 50 | C-2 10 | 80 | 2.7 | 48 | 220 | 10.8 | 1.6 | | One out of seven subjects suffered from slight prickly heat. | |
| 2 | A-2 40 | B-1 50 | C-1 10 | 80 | 2.5 | 28 | 140 | 14.0 | 1.7 | | All seven subjects showed no abnormality. | |
| 3 | A-1 45 | B-1 50 | C-2 5 | 80 | 2.7 | 38 | 240 | 9.5 | 1.2 | | Two out of seven subjects suffered from slight prickly heat. | |
| 4 | A-1 30 | B-1 50 | C-2 20 | 80 | 2.7 | 36 | 136 | 5.4 | 1.5 | | | |
| 5 | A-1 70 | B-1 20 | C-2 10 | 80 | 2.7 | 35 | 256 | 18.3 | 0.2 | | Three out of seven subjects had a diaper rash like prickly heat. | |
| 6 | A-1 55 | B-1 35 | C-2 10 | 80 | 2.7 | 37 | 233 | 12.6 | 0.5 | | | |
| 7 | A-1 30 | B-1 60 | C-2 10 | 80 | 2.7 | 33 | 148 | 4.8 | 1.7 | | Half of the diapers tested were torn during the use test. | |
| 8 | A-1 40 | B-1 50 | C-1 10 | 80 | 2.7 | 35 | 215 | 9 | 1.4 | | | |
| 9 | A-1 40 | B-1 50 | C-1 10 | 80 | 1.5 | 45 | 241 | 12.5 | 0.6 | | | Nonuniformly stretched |
| 10 | A-1 40 | B-1 50 | C-1 10 | 80 | 1.2 | 50 | 289 | 13.3 | 0.2 | | | Nonuniformly stretched |
| 11 | A-1 40 | B-2 50 | C-2 10 | 80 | 2.7 | 35 | 219 | 7.1 | 1.3 | | | |
| 12 | A-1 40 | B-3 50 | C-2 10 | 80 | 2.7 | 36 | 231 | 7.8 | 1.4 | | | |
| 13 | A-2 45 | B-1 50 | C-1 5 | 80 | 2.5 | 30 | 183 | 9.5 | 1.8 | | | |
| 14 | A-2 40 | B-1 50 | C-1 10 | 80 | 2.5 | 30 | 195 | 15.2 | 0.4 | | | |
| 15 | A-2 55 | B-1 35 | C-1 10 | 80 | 2.5 | 29 | 120 | 5.6 | 2.0 | | 25% of the diapers tested were torn during the use test. | |
| 16 | A-2 30 | B-2 60 | C-3 10 | 80 | 2.5 | 30 | 145 | 9.4 | 1.9 | | | |
| 17 | A-2 40 | B-3 50 | C-3 10 | 80 | 2.5 | 31 | 148 | 10.3 | 2.2 | | | |
| 18 | A-2 40 | B-1 50 | C-4 10 | 80 | 2.5 | 30 | 154 | 9.1 | 1.8 | | | |
| 1 | A-1 40 | B-1 50 | C-4 10 | 110 | 4.0 | 25 | 134 | 3.2 | 1.5 | | The diaper was torn during its forming work. | |
| 2 | A-1 50 | B-1 50 | C-4 10 | 110 | 4.0 | 35 | 165 | 4.5 | 1.2 | | The diaper was torn during its use test. | |
| 3 | A-1 50 | B-1 50 | C-4 10 | 110 | 6.0 | 25 | 126 | 2.4 | 1.6 | | The diaper was torn during its forming work. | |
| 4 | A-2 30 | B-1 60 | C-4 10 | 100 | 6.0 | 25 | 102 | 3.3 | 1.7 | | The diaper was torn during | |

TABLE 1-continued

| | Composition (*) | | | Stretching conditions | | Film thickness (μ) | Strength | | Moisture permeability g/100 cm².2 hr | Flexibility | Disposable diaper formability and use test | Remarks |
|---|---|---|---|---|---|---|---|---|---|---|---|---|
| | Polyolefin resin | Filler | Hydrocarbon polymer | Temperature (°C.) | Stretch ratio | | Tensile strength (g) | Tear strength (g) | | | | |
| | | | | | | | | | | | its forming work. | |
| 5 | 50 A-2 | 50 B-1 | 10 C-4 | 100 | 6.0 | 33 | 124 | 4.7 | 1.5 | | The diaper was torn during its use test. | |
| 6 | 50 A-2 | 50 B-1 | 10 C-4 | 100 | 6.0 | 37 | 143 | 4.8 | 1.1 | | The diaper was torn during its use test | |
| 7 | 50 | 50 | 10 | — | — | 26 | 250 | 50 | 0.03 | | Five out of seven subjects had a diaper rash like prickly heat. | Using commercially available leakproof film. |
| 8 | — | — | — | — | — | — | — | — | 1.6 | | One out of seven subjects suffered from slight prickly heat. | Using two sheets of wool flannel and a commercially available diaper cover |

(*)part by weight

TABLE 2

| Sign | Meaning |
|---|---|
| A-1 | High-density polyethylene, Novatek ER002 (Mitsubishi Kasei Kogyo) |
| A-2 | Linear low-density polyethylene, Ultzex 2021-NF (Mitsui Sekiyu Kagaku) |
| B-1 | Calcium carbonate, average particle size = 1.2µ, treated with a fatty acid |
| B-2 | Talc, MS talc (Japan Talc) |
| B-3 | Diatomaceous earth |
| C-1 | Wax-like hydrocarbon polymer prepared by hydrogenating hydroxyl-terminated polybutadiene (Preparation 1) |
| C-2 | Liquid hydrocarbon polymer prepared by hydrogenating hydroxyl-terminated polybutadiene (Preparation 2) |
| C-3 | Liquid polybutadiene, Nisso PBG (Nippon Soda) |
| C-4 | Liquid polybutene, Nisseki Polybutene HV-300 (Nippon Sekiyu Kagaku) |

From Table 1, an obvious difference is seen in film flexibility between Example 1 of this invention and Comparative Examples 1–3. It is noted that in the case of the comparative examples (known paper diapers), troubles arise during their forming work and the diapers, even if well formed, become torn during use. Example 2 is a diaper made by using a linear low-density polyethylene resin. Its difference from Comparative Examples 4–6 in film flexibility is evident. The diapers of Examples 3–7 were made by using a high-density polyethylene and varying the proportions of the resin, filler and hydrocarbon polymer. The limit blending proportions of the respective three components can be deduced from these Examples. In Examples 1 and 8–10, the film working conditions were varied to change the thickness of the produced porous film. In these examples, although an improvement of film strength is noted, both flexibility and moisture permeability are reduced. Thus, the allowable limits of film thickness can be determined from these results. Examples 11 and 12 are cases wherein talc and diatomaceous earth were used as filler. It is seen that the films obtained in these examples show properties equal to those of the film of Example 1. In Examples 2 and 13–18, porous films were produced by using linear low-density polyethylene and diapers were similarly made by using these films. It is noted that linear low-density polyethylene is preferable to high-density polyethylene in flexibility and moisture permeability of the film. Comparative Example 7 is a disposable diaper made by using a commercially available back film. Five of the seven subjects who used this diaper had diaper rash in two days' use. Comparative Example 8 is a diaper (baby pants) made from commercially available wool flannel. In the use test thereof, two pieces of commercially available diaper of ring-shaped bleached cotton cloth were used therewith. In all the use tests, the timing of changing the diapers was left to the discretion of the test subjects' mothers.

As is apparent from the foregoing results, the disposable diaper according to this invention shows excellent practical utility.

We claim:

1. In a disposable diaper comprising an integral assembly of a liquid-impermeable back sheet, an absorbent medium placed thereon and a liquid-permeable sheet overlying said absorbent medium, the improvement which comprises: said back sheet is a porous, vapor-permeable, liquid-impermeable film made by mixing 100 parts by weight of a polyolefin resin, 28, to 200 parts by weight of filler particles and 10 to 70 parts by weight of a liquid or wax-like hydrocarbon polymer said polymer being a saturated hydroxy-substituted hydrocarbon polymer obtained by hydrogenating hydroxy-substituted liquid polybutadiene having from 1.5 to 5 hydroxyl groups per molecule, said hydroxy-substituted hydrocarbon polymer having a number average molecular weight of from 400 to 48,000, molding the mixture to form a film and then stretching said film more than 1.2 times its original dimension in at least one surface direction to form fine pores in the film.

2. The disposable diaper according to claim 1, wherein said polyolefin resin is high-density polyethylene.

3. The disposable diaper according to claim 1, wherein said polyolefin resin is linear low-density polyethylene resin.

4. The disposable diaper according to claim 1 in which said film consists essentially of from 30 to 55% by weight of said resin, from 35 to 55% by weight of said filler and from 5 to 20% by weight of said hydrocarbon polymer.

5. The disposable diaper according to claim 1 in which said back sheet consists essentially of said film.

6. The disposable diaper according to claim 1 in which said polyolefin resin is selected from the group consisting of low-density polyethylene and high-density polyethylene.

7. The disposable diaper according to claim 6 in which the film is stretched from 1.2 to 4.0 times its original dimension in at least one surface direction.

8. The disposable diaper according to claim 6 in which said filler particles have a particle size in the range of from 1 to 5 microns.

9. The disposable diaper according to claim 6 in which said film has a basis weight of from 20 to 50 g/m$^2$.

10. In a disposable diaper comprising an integral assembly of a liquid-impermeable back sheet, an absorbent medium placed thereon and a liquid-permeable sheet overlying said absorbent medium, the improvement which comprises: said back sheet is a porous, vapor-permeable, liquid-impermeable film made by mixing (1) 100 parts by weight of a polyolefin resin selected from the group consisting of high-density polyethylene resin, polypropylene resin, linear low-density polyethylene resin and mixtures thereof, (2) 28 to 200 parts by weight of filler particles having a particle size of from 1 to 5 microns, said filler particles having been surface treated with a fatty acid or metal salt thereof to improve the dispersibility of said filler particles in said resin, and (3) 10 to 70 parts by weight of a liquid or wax-like hydrocarbon polymer, said polymer being a saturated polyhydroxy-substituted hydrocarbon polymer having a number-average molecular weight of from 400 to 48000 and obtained by hydrogenating hydroxy-terminated liquid polybutadiene until it is substantially saturated, said hydrocarbon polymer having from 2.0 to 5.0 hydroxyl groups per molecule; molding the mixture to form a film and then stretching said film from 1.2 to 4.0 times its original dimension in at least one surface direction to form fine pores in the film.

* * * * *